United States Patent
Griesbach et al.

(10) Patent No.: US 8,614,358 B2
(45) Date of Patent: Dec. 24, 2013

(54) PROCESS FOR PREPARING 2-METHYL-3-(4-TERT-BUTYLPHENYL) PROPANAL WITH HIGH PARA-ISOMER PURITY

(75) Inventors: Ulrich Griesbach, Mannheim (DE); Jörg Botzem, Limburgerhof (DE); Florian Stecker, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/234,809

(22) Filed: Sep. 16, 2011

(65) Prior Publication Data

US 2012/0071696 A1    Mar. 22, 2012

Related U.S. Application Data

(60) Provisional application No. 61/383,355, filed on Sep. 16, 2010.

(51) Int. Cl.
*C07C 45/42* (2006.01)

(52) U.S. Cl.
USPC .......................................... 568/426; 568/423

(58) Field of Classification Search
USPC ................................. 568/426, 433
See application file for complete search history.

(56) References Cited

U.S. PATENT DOCUMENTS

| | | | |
|---|---|---|---|
| 2,875,131 A | 2/1959 | Carpenter | |
| 4,318,783 A | 3/1982 | Buhmann et al. | |
| 5,208,384 A | 5/1993 | Hermeling | |
| 5,507,922 A | 4/1996 | Hermeling et al. | |
| 6,723,883 B1 | 4/2004 | Therre et al. | |
| 2005/0202967 A1 | 9/2005 | Hoefer et al. | |
| 2012/0016162 A1 | 1/2012 | Stecker et al. | |

FOREIGN PATENT DOCUMENTS

| | | |
|---|---|---|
| DE | 41 06 661 A1 | 9/1992 |
| DE | 102 23 970 A1 | 12/2003 |
| DE | 102004011427 A1 | 9/2005 |
| EP | 0 012 240 A2 | 6/1980 |
| EP | 0 045 571 A1 | 2/1982 |
| EP | 0 638 665 A1 | 2/1995 |
| WO | WO-01/27061 A1 | 4/2001 |
| WO | WO-2009/059944 A1 | 5/2009 |
| WO | WO-2012/034930 A1 | 3/2012 |

OTHER PUBLICATIONS

Bosma, et al., "Anodic oxidation of 4-t-butyltoluene to 4-t-butylbenzaldehyde dimethyl acetal: optimization and scale-up" South African Journal of Chemistry (1999) pp. 133-144.
International Search Report for PCT/EP2011/065596 mailed Jan. 25, 2012.
Moritz, et al., XP002666752, Chem. Ber., vol. 32 (1899) pp. 2531-2534.

*Primary Examiner* — Sikarl Witherspoon
(74) *Attorney, Agent, or Firm* — Novak Druce Connolly Bove + Quigg LLP

(57) ABSTRACT

The present invention relates to a process for preparing 2-methyl-3-(4-tert-butyl-phenyl)propanal with high para-isomer purity, and also to a process for preparing 4-tert-butylbenzaldehyde with high para-isomer purity.

19 Claims, No Drawings

PROCESS FOR PREPARING 2-METHYL-3-(4-TERT-BUTYLPHENYL)PROPANAL WITH HIGH PARA-ISOMER PURITY

CROSS-REFERENCE TO RELATED APPLICATIONS

This application claims the benefit of U.S. Provisional Application 61/383,355, filed on Sep. 16, 2010, which is incorporated by reference.

BACKGROUND OF THE INVENTION

The present invention relates to a process for preparing 2-methyl-3-(4-tert-butyl-phenyl)propanal with high para-isomeric purity, and also to a process for preparing 4-tert-butylbenzaldehyde with high para-isomeric purity.

2-Methyl-3-(4-tert-butylphenyl)propanal is in particular used as lily-of-the-valley fragrance, and the protected trademarks Lysmeral®, Lilial®, or Lilestralis® are often used to refer to the material in this connection. Because of the production process used, marketed 2-methyl-3-(4-tert-butylphenyl)propanal of the formula (I) always also comprises 2-methyl-3-(3-tert-butylphenyl)propanal of the formula (II).

There are a number of known processes that can give compound (I) or a mixture of compounds (I) and (II). By way of example, the specification EP 0 045 571 teaches that the compounds (I) and (II) can be accessed starting from benzaldehyde via condensation with propanal and subsequent hydrogenation of the α,β-unsaturated aldehyde to give 2-methyl-3-phenyl-1-propanol.

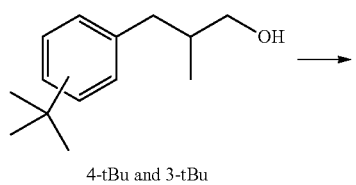

4-tBu and 3-tBu

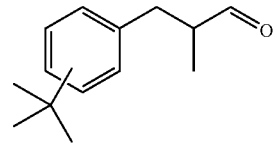

(I) 4-tBu
(II) 3-tBu

The ratio between the corresponding para-isomeric and the meta-isomer can be adjusted to a certain extent by controlling the reaction conditions during introduction of the tert-butyl moiety into the 2-methyl-3-phenyl-1-propanol. The two isomeric alcohols are then dehydrogenated to give the target compounds (I) and (II).

WO 2001/027061 and the references cited therein describe another process for preparing 2-methyl-3-(4-tert-butylphenyl)propanal.

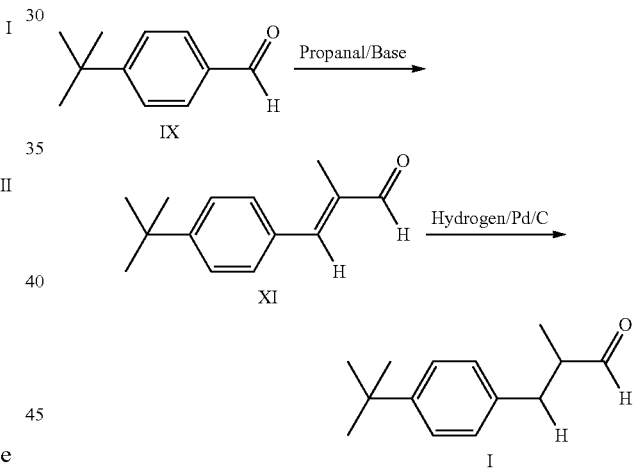

EP 0 638 665 and the references cited therein describe the synthesis of the diacetal of the formula VII, which can be converted via hydrolysis to the corresponding aldehyde of the formula IX, where the diacetal of the formula VII is obtained via electrochemical oxidation of 4-tert-butyltoluene of the formula III.

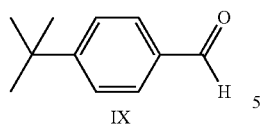

IX

The 2-methyl-3-(4-tert-butylphenyl)propanal prepared as in WO 2001/027061 usually comprises about 0.5 to 2% by weight of the corresponding meta-isomer of the formula II, namely 2-methyl-3-(3-tert-butylphenyl)propanal, based on the total mass of the compounds of the formulae I and II, since the 4-tert-butyltoluene used as starting material comprises about 1 to 5% by weight of 3-tert-butyltoluene of the formula IV, based on the total mass of the compounds of the formulae III and IV.

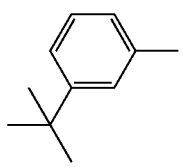

IV

DE 102 23 970 describes the use of a partitioned column for distillative purification of 2-methyl-3-(4-tert-butylphenyl)propanal of the formula I from a crude mixture, whereupon a 2-methyl-3-(4-tert-butylphenyl)propanal with less than 1.0% by weight content of impurities was isolated.

The presence of from 0.2 to 70% by weight content of 2-methyl-3-(3-tert-butyl-phenyl)propanal (formula II) in the product mixture has not hitherto impaired the fragrance properties of 2-methyl-3-(4-tert-butylphenyl)propanal (formula I). C. Sell, Angew. Chem. 2006, 118, 6402-6410, describes 2-methyl-3-(3-tert-butyl-phenyl)propanal (formula II) as having a more intensive odor than 2-methyl-3-(4-tert-butylphenyl)propanal (formula I). A certain content of 2-methyl-3-(3-tert-butyl-phenyl)propanal (formula II) has therefore actually been desirable in fragrance compositions comprising the abovementioned lily-of-the-valley fragrances used in perfume applications.

However, a change in the requirements of the market has made it necessary to reduce the content of auxiliary components in 2-methyl-3-(4-tert-butylphenyl)propanal (formula I), in particular 2-methyl-3-(3-tert-butylphenyl)propanal (formula II), and the content of undesired 2-methyl-3-(3-tert-butylphenyl)propanal (formula II) in the 2-methyl-3-(4-tert-butylphenyl)propanal (formula I) prepared by the processes described above, usually more than 0.5% by weight, based on the total mass of the compounds of the formulae I and II, is therefore significantly too high.

BRIEF SUMMARY OF THE INVENTION

It was therefore an object of the present invention to provide a process which is simple and which is easy to implement, and which provides access to 2-methyl-3-(4-tert-butylphenyl)propanal (formula I) with isomeric purity such that the content of 2-methyl-3-(3-tert-butylphenyl)propanal (formula II) in the 2-methyl-3-(4-tert-butylphenyl)propanal (formula I) prepared is significantly smaller than in the products hitherto commercially available, while avoiding any drastic reduction of the cost-effectiveness of the process.

Said object is achieved via a process for preparing 2-methyl-3-(4-tert-butyl-phenyl)propanal of the formula I

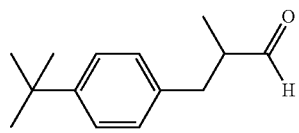

I with less than 0.3% by weight content of 2-methyl-3-(3-tert-butylphenyl)propanal of the formula II, preferably less than 0.1% by weight,

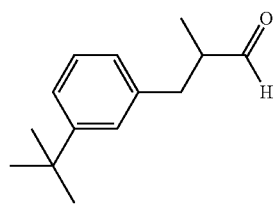

II based on the total mass of the compounds of the formulae I and II starting from 4-tert-butyltoluene of the formula III

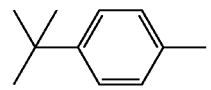

III with at most 5% by weight, preferably from 0.01 to 5% by weight, in particular from 0.1 to 5% by weight, in particular from 0.5 to 5% by weight, content of 3-tert-butyltoluene of the formula IV

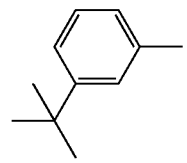

IV based on the total mass of the compounds of the formulae III and IV, as starting material, comprising the steps of:

a) electrochemical anodic methoxylation of a mixture comprising compounds of the formulae III and IV, and also comprising the benzyl ethers of the formulae V and VI which are produced as intermediates

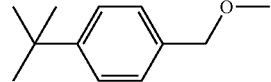

V

-continued

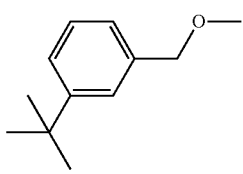

VI to give the dimethyl acetals of the formulae VII and VIII

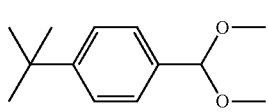

VII

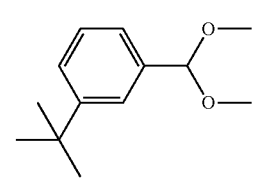

VIII in an electrolysis solution comprising methanol, at least one conducting salt, and also optionally one cosolvent or a plurality of various cosolvents;

b) hydrolysis of the mixture of the dimethyl acetals of the formulae VII and VIII formed in step a) to give the corresponding benzaldehydes of the formulae IX and X

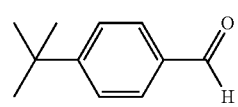

IX

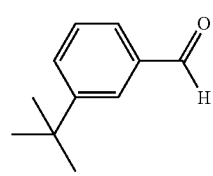

X and then use of distillation to reduce the concentration of the benzaldehyde of the formula X;

c) reaction of the mixture of the benzaldehydes of the formulae IX and X obtained in step b), where the mixture comprises less than 0.5% by weight, preferably less than 0.3% by weight, of the benzaldehyde of the formula X, with propanal under basic conditions to give the dehydrocinnamaldehydes of the formulae XI and XII;

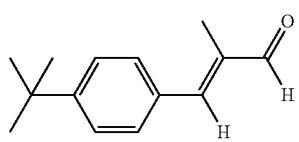

XI

-continued

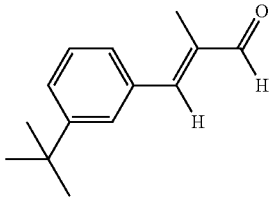

XII d) catalytic hydrogenation of the dehydrocinnamaldehydes of the formulae XI and XII prepared in step c) to give the propanals of the formulae I and II,

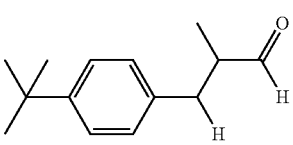

I

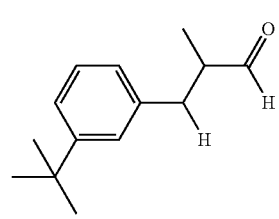

II where the content of the propanal of the formula II is less than 0.3% by weight, based on the total mass of the compounds of the formulae I and II, and then optionally use of distillation to remove solvent residues, precursors, and byproducts;

e) optionally final distillation of the propanals of the formulae I and II obtained in step d), in order to reduce the concentration of the propanal of the formula II.

DETAILED DESCRIPTION OF THE INVENTION

In step a) of the process of the invention, a mixture comprising 4-tert-butyltoluene of the formula III

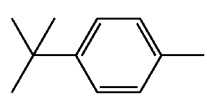

III with at most 5% by weight, preferably from 0.01 to 5% by weight, in particular from 0.1 to 5% by weight, in particular from 0.5 to 5% by weight, content of 3-tert-butyltoluene of the formula IV

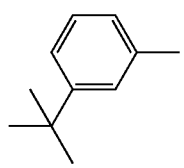

IV based on the total mass of the compounds of the formulae III and IV, as starting material, and also the benzyl ethers of the formulae V and VI produced as intermediates,

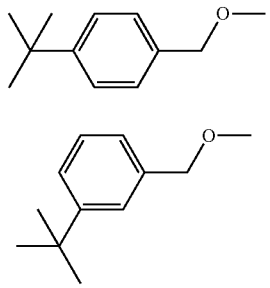

V

VI are converted via electrochemical anodic methoxylation to give the dimethyl acetals of the formulae VII and VIII in an electrolysis solution comprising methanol, at least one conducting salt, and also optionally one cosolvent or a plurality of various cosolvents.

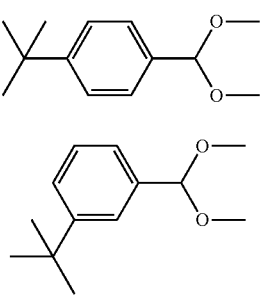

VII

VIII

The electrochemical anodic methoxylation of toluene derivatives is in principle known and is described by way of example in EP 0 638 665 and in the references cited therein, for example in DE-A 41 06 661 and EP 0 012 240, and also in the following documents: H. Putter, (2001) Industrial electroorganic chemistry., H. L and, O. Hamerich (eds.) Organic electrochemistry, 4th ed., Marcel Dekker, New York, N.Y. 2001, pp. 1259-1307, and also P. Loyson, S. Gouws, B. Zeelie, S. Afr. J. Chem., 2002, 55, 125-131, and P. Loyson, S. Gouws, B. Barton, M. Ackermann, S. Afr. J. Chem., 2004, 57, 53-56 and in the references described therein, where the abovementioned documents, and also all of the other documents cited in the present application, are incorporated by reference in their entirety into the present disclosure.

For the purposes of the process of the invention, the electrolysis solution comprises not only the starting materials of the formulae III and IV (toluenes), and also the benzyl ethers of the formulae V and VI produced as intermediates, but also at least methanol, and also at least one conducting salt.

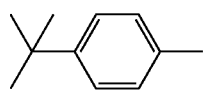

III

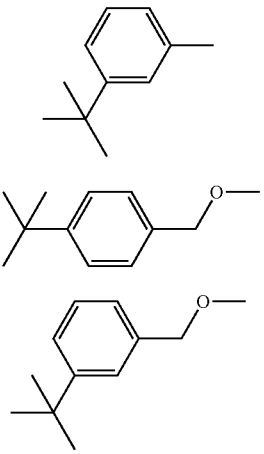

IV

V

VI

The conducting salts that can be comprised within the electrolysis solution are generally alkali metal salts or tetra ($C_1$-$C_6$-alkyl)ammonium salts, preferably tri($C_1$-$C_6$-alkyl) methylammonium salts. Counterions that can be used are sulfate, hydrogensulfate, alkyl sulfates, aryl sulfates, alkylsulfonates, arylsulfonates, halides, phosphates, carbonates, alkyl phosphates, alkyl carbonates, nitrate, alcoholates, tetrafluoroborate, or perchlorate.

The acids derived from the abovementioned anions can also be used as conducting salts, examples of these being sulfuric acid, sulfonic acids, and also carboxylic acids.

Other suitable conducting salts are ionic liquids. Suitable ionic liquids are described in "Ionic Liquids in Synthesis", eds. Peter Wasserscheid, Tom Welton, Verlag Wiley VCH, 2003, chapters 1 to 3, and also in DE-A 102004011427.

The conducting salts preferred in step a) of the process of the invention are methyltributylammonium methyl sulfate (MTBS), methyltriethylammonium methyl sulfate, sodium methyl sulfate, sodium ethanesulfonate, and sulfuric acid.

For the purposes of one advantageous embodiment of step a) of the process of the invention, the concentration of the conducting salt in the electrolysis solution is usually selected within the range from 0.1 to 30 percent by weight (% by weight), preferably within the range from 0.2 to 10% by weight, particularly preferably from 0.25 to 4% by weight. All % by weight data are based on the total weight of the electrolysis solution.

Another preferred embodiment of step a) of the process of the invention is one wherein the electrochemical anodic methoxylation is carried out at an electrolysis-solution temperature in the range from 35 to 70° C., in particular in the range from 45 to 60° C.

Step a) of the process of the invention is moreover preferably carried out in such a way that the electrochemical anodic methoxylation is carried out at an absolute pressure in the range from 500 to 100 000 mbar, preferably at an absolute pressure in the range from 1000 to 4000 mbar.

Conventional cosolvents are optionally added to the electrolysis solution. These are the high-oxidation-potential inert solvents well-known in organic chemistry. By way of example, mention may be made of dimethyl carbonate or propylene carbonate. For the purposes of one preferred embodiment, step a) of the process of the invention is therefore carried out in the presence of dimethyl carbonate and/or propylene carbonate as cosolvents.

In principle, water is also suitable as cosolvent, the proportion of water in the electrolyte (=electrolysis solution) preferably being at most 20% by weight, in particular at most 10% by weight, preferably at most 5% by weight, in particular at most 0.05% by weight.

Another preferred embodiment of step a) of the process of the invention uses an electrolyte (=electrolysis solution) of which the water content is usually in the range from 0.001 to 5% by weight, preferably in the range from 0.01 to 1% by weight, particularly preferably in the range from 0.01 to 0.5% by weight. All % by weight data are based on the total weight of the electrolysis solution at the start of the reaction.

The present invention also comprises the discovery that it is advantageous, during the entire step a), that the water content of the electrolysis solution is at most 20% by weight, in particular at most 10% by weight, preferably at most 5% by weight, in particular at most 0.05% by weight, in particular at most 0.01% by weight.

The proportions of water can be determined by various methods known from the literature. A particularly suitable method is Karl Fischer titration. The water can have been added as cosolvent to the electrolyte, or can derive from one of the starting materials, such as methanol or sulfuric acid, or can be introduced into the synthesis (see by way of example step 2.3 in example 2) via the return of tert-butylbenzaldehyde. If tert-butylbenzaldehyde is returned to the electrochemical methoxylation process (step a)), the tert-butylbenzaldehyde is acetalized in the acidic medium (pH<7) of the electrolyte to give the corresponding tert-butylbenzaldehyde dimethyl acetal, with liberation of one equivalent of water. It is preferable that the water produced during the acetalization of tert-butylbenzaldehyde is removed from the equilibrium.

The water can be removed by distillation, preferably via use of solvent and/or entrainer, e.g. toluene or methanol.

Another possibility for removing water from the electrolyte consists in the use of dewatering agents, such as orthoesters.

In one preferred embodiment of the invention, the electrolysis solution in step a) comprises from 0.1 to 10% by weight of an orthoester or a mixture of various orthoesters. The % by weight data are based on the total weight of the electrolysis solution.

In one preferred embodiment of the present invention, the electrolysis solution in step a) comprises not only methanol, at least one conductive salt, and also optionally a cosolvent or a plurality of various cosolvents, but also from 0.1 to 10% by weight, based on the total weight of the electrolysis solution, preferably from 0.2 to 5% by weight, very particularly preferably from 0.5 to 5% by weight, of an orthoester or a mixture of various orthoesters.

Orthoesters are alkyl and aryl esters of orthocarboxylic acids, which are not known in unesterified form, the esters therefore being compounds of the general formula $R_1-C(OR_2)_3$, where $R_1$ is H or C1 to C6 alkyl moieties, and $R_2$ is mutually independently C1 to C6 alkyl moieties.

Examples of suitable orthoesters are orthoformic esters (orthoformates) ($R_1$=H) and orthoacetic esters (orthoacetates, $R_1$=$CH_3$), and also mixtures thereof.

Examples of suitable orthoformic esters are trimethyl orthoformate ($R_1$=H, $R_2$=$CH_3$) and triethyl orthoformate ($R_1$=H, $R_2$=$C_2H_5$).

Examples of suitable orthoacetic esters are trimethyl orthoacetate ($R_1$=$CH_3$, $R_2$=$CH_3$) and triethyl orthoacetate ($R_1$=$CH_3$, $R_2$=$C_2H_5$).

It is preferable to use trimethyl orthoformate ($R_1$=H, $R_2$=$CH_3$) or trimethyl orthoacetate ($R_1$=$CH_3$, $R_2$=$CH_3$), and it is very particularly preferable to use trimethyl orthoformate ($R_1$=H, $R_2$=$CH_3$).

The resultant by-products methyl acetate and ethyl acetate, and methyl formate and ethyl formate, can then easily be removed from the reaction mixture by distillation in a subsequent step. It is preferable to use trimethyl orthoformate (trimethoxymethane, CAS 14-73-5).

In one preferred embodiment of the invention, the amount of orthoester is selected in such a way that the molar ratio of orthoester to the entirety of the tert-butylbenzaldehydes comprised in the electrolysis solution (via addition or return) is in the range from 0.1 to 1.5:1, preferably in the range from 0.1 to 1:1.

In one embodiment, the orthoester, such as trimethyl orthoformate, is metered in portions and/or continuously into the electrolyte.

Another possibility for removing water from the electrolyte consists in the use of ion exchangers or molecular sieves. Ion exchangers and molecular sieves are known per se. Molecular sieves are preferably selected from naturally occurring and synthetic zeolites, where these can take the form of spheres (beads), of powder, or of elongate pellets. It is preferable to use 4 Å molecular sieve, and it is particularly preferable to use 3 Å molecular sieve.

In one embodiment of the present invention, molecular sieve or preferably ion exchanger is admixed with the electrolytes from step a), and the molecular sieve and, respectively, the ion exchanger is allowed to act on the electrolytes; an example of a method for this stirs the suspension of molecular sieve and, respectively, ion exchanger in the electrolyte, and specifically continuously or during defined intervals. Instead of stirring, it is also possible to use shaking or pumped circulation, until the water content reached is <0.5% by weight. Once molecular sieve or ion exchanger has acted on the electrolytes it is necessary to remove the molecular sieve and, respectively, the ion exchanger. They can be removed by distillation or decanting of the electrolyte, or preferably by filtration.

In one embodiment of the invention, prior to step a), the electrolysis solution is dried over molecular sieve, preferably over 4 Å molecular sieve, particularly preferably over 3 Å molecular sieve, until water content is at most 0.05% by weight, and the molecular sieve is removed from the electrolyte by filtration prior to step a).

After the molecular sieves used for water removal have been removed they can be regenerated (e.g. by passing a stream of hot air through the same or heating the same in vacuo) and reused. These processes are known to the person skilled in the art.

Examples of advantages of the use of electrolytes with reduced water content, rather than electrolytes that are otherwise identical but have not been dried or have been only partially dried, in the electrochemical methoxylation process are higher selectivity of the reaction, and also lower specific electrical energy consumption, based on useful product (in kg).

Step a) of the process of the invention can be carried out in any of the conventional divided or undivided types of electrolysis cell. It can be carried out with good results either batchwise or continuously. For the purposes of one preferred embodiment, step a) of the process of the invention is carried out continuously. It is preferable to operate continuously with undivided through-flow cells.

Very particularly suitable cells are bipolar capillary cells or plate-stack cells, where the electrodes are configured as plates and have been arranged parallel to one another (Ullmann's Encyclopedia of Industrial Chemistry, 1999 electronic release, Sixth Edition, VCH-Verlag Weinheim, Volume Electrochemistry, Chapter 3.5 Special cell designs, and also Chapter 5, Organic Electrochemistry, Subchapter 5.4.3.2 Cell Design). Preferred electrode materials are noble metals, such as platinum, mixed-oxide electrodes, such as $RuO_xTiO_x$ (known as DSA electrodes), or carbon-containing materials, such as graphite, glassy carbon, or diamond electrodes. It is very particularly preferable to use graphite electrodes. For the purposes of one preferred embodiment, step a) of the process of the invention is carried out with use of a plate-stack cell.

The current densities used for carrying out step a) are generally from 1 to 1000 $mA/cm^2$, preferably from 10 to 100 $mA/cm^2$. It is particularly preferable to carry out step a) of the process of the invention at current densities of from 10 to 50 $mA/cm^2$. Operations are generally carried out at atmospheric pressure. Higher pressures are preferably used when the intention is to operate at relatively high temperatures, the aim being to avoid boiling of the starting compounds or of the solvent.

Examples of suitable anode materials are noble metals, such as platinum or metal oxides, such as ruthenium oxide or chromium oxide, or mixed oxides of the $RuO_x$ or $TiO_x$ type, or else diamond electrodes. Preference is given to graphite or carbon electrodes.

Examples of cathode materials that can be used are iron, steel, stainless steel, nickel, or noble metals, such as platinum, and also graphite or carbon materials, and diamond electrodes. Preference is given to a system having graphite as anode and cathode, or else graphite as anode and nickel, steel, or stainless steel as cathode.

Preference is given to a process of the invention in which the 4-tert-butyltoluene of the formula III used as starting material in step a) has from 2 to 4% by weight content of 3-tert-butyltoluene of the formula IV, particularly from 2.5 to 3.5% by weight, based on the total mass of the compounds of the formulae III and IV. Alongside the 4-tert-butyltoluene respectively used as fresh starting material, it is also possible that the unreacted and reclaimed starting materials of the formulae III and IV, and also the benzyl ethers of the formulae V and VI formed as intermediates are added to the fresh 4-tert-butyltoluene of the formula III used for the first time in step a) with at most 5% by weight, preferably from 0.01 to 5% by weight, in particular from 0.1 to 5% by weight, in particular from 0.5 to 5% by weight, preferably from 2 to 4% by weight, particularly preferably from 2.5 to 3.5% by weight, content of 3-tert-butyltoluene of the formula IV. The content of 3-tert-butyltoluene of the formula IV within the 4-tert-butyltoluene of the formula III reclaimed in step b) usually differs from the content of 3-tert-butyltoluene present in the fresh 4-tert-butyltoluene used.

In step b) of the process of the invention, the mixture formed in step a) of the dimethyl acetals of the formulae VII and VIII is hydrolyzed to give the corresponding benzaldehydes of the formulae IX and X

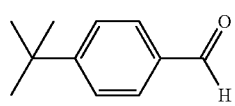

IX

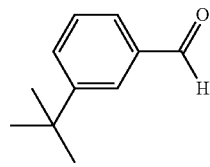

X and then distillation is used to reduce the concentration of the benzaldehyde of the formula X.

The hydrolysis of the dimethyl acetals of the formulae VII and VIII to give the corresponding benzaldehydes of the formulae IX and X in the presence of water in acidic conditions is in principle known and is described by way of example in H. Putter, (2001) Industrial electroorganic chemistry, and in H. Lund, O. Hamerich (eds.) Organic electrochemistry, 4th ed., Marcel Dekker, New York, N.Y. 2001, pp. 1288-1289, or K. Schwetlick, Organikum, 21st edition 2001, Wiley-VCH, Weinheim, p. 182.

Distillation is used to remove the undesired benzaldehyde of the formula X. It is preferable here that a benzaldehyde of the formula IX is obtained which has less than 0.5% by weight, preferably less than 0.3% by weight, preferably less than 0.2% by weight, in particular less than 0.1% by weight, content of the benzaldehyde of the formula X, based on the total mass of the compounds of the formulae IX and X.

The distillation carried out in step b) can take place in one stage, two stages, or else a plurality of stages, and the column types known to the person skilled in the art can be used here.

Preference is given to a process of the invention in which the mixture of the benzaldehydes of the formulae IX and X obtained after the distillation in step b) has less than 0.1% by weight content of the benzaldehyde of the formula X, based on the total mass of the compounds of the formulae IX and X.

Particular preference is given to a process of the invention in which the distillation in step b) is carried out in two stages, by using a 1st distillation column in a first distillation to remove, at the top of the 1st distillation column, a distillate which comprises more than 80% by weight of a mixture composed of unreacted starting materials of the formulae III and IV, and also of the benzyl ethers of the formulae V and VI produced as intermediates in step a), and of the benzaldehyde of the formula X,

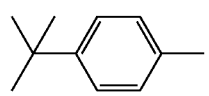

III

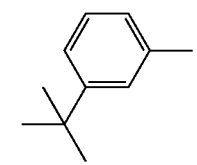

IV

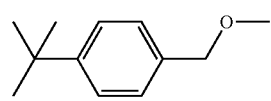

V

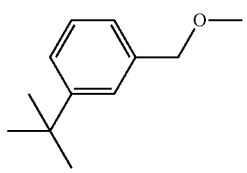

VI

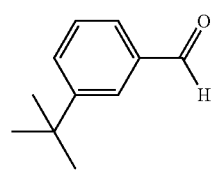

X and using a 2nd distillation column in a second distillation to remove, at the top of the 2nd distillation column, the benzaldehyde of the formula IX

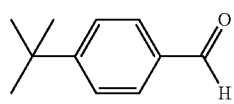

IX with less than 0.5% by weight, preferably less than 0.1% by weight, content of the benzaldehyde of the formula X, based on the total mass of the compounds of the formulae IX and X, from the bottom product of the first distillation, and where optionally the distillate which is obtained at the top of the 1st distillation column and which comprises the compounds of the formulae III, IV, V, VI, and X, is reused in step a) together with the 4-tert-butyltoluene of the formula III that is used as starting material.

It is preferable that the 1st distillation column used in step b) has more than 40 theoretical plates, in particular more than 50. The columns preferably have commercially available metal gauze packings, of the type obtainable from Montz or Sulzer.

The preferred two-stage distillation can in principle also be executed in a single partitioned column. However, preference is given to distillation in which the two distillation steps are executed separately from one another, particularly preferably in two different distillation columns respectively adapted to the specific separation requirements.

In step c), the mixture obtained of the benzaldehydes of the formulae IX and X in step b), where the mixture comprises less than 0.5% by weight, preferably less than 0.3% by weight, of the benzaldehyde of the formula X, is reacted with propanal under basic conditions to give the dehydrocinnamaldehydes of the formulae XI and XII.

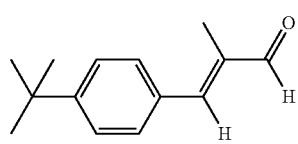

XI

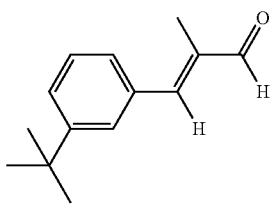

XII

In step d), the dehydrocinnamaldehydes of the formulae XI and XII prepared in step c) are catalytically hydrogenated to give the propanals of the formulae I and II,

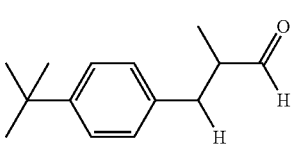

I

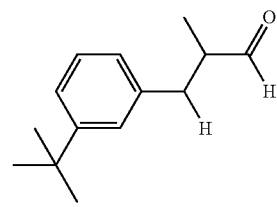

II where the content of the propanal of the formula II is less than 0.3% by weight, based on the total mass of the compounds of the formulae I and II, optionally with subsequent use of distillation to remove solvent residues, precursors, and byproducts.

In step e) the propanals of the formulae I and II obtained in step d) are optionally subjected to a final distillation in order to reduce the concentration of the propanal of the formula II.

Steps c) and d) are usually carried out as described in WO 2001/027061 or in H. Surburg, J. Panten, Common Fragrance and Flavor Materials, 5th edition, Wiley-VCH, Weinheim 2006, pp. 115-117.

Preference is given to a process of the invention in which, in step d), the crude product from the catalytic hydrogenation is subjected to a distillation to remove solvent residues, precursors, and byproducts.

If the resultant propanal of the formula I still has excessive content of the propanal of the formula II, the concentration of propanal of the formula II can be further reduced via a final distillation. This type of final distillation is preferably carried out in a partitioned column, for example of the type described in DE10223970.

Particular preference is given to a process of the invention in which the mixture of the propanals of the formulae I and II obtained after the distillation in step d) or e) has less than 0.05% by weight content of the propanal of the formula II, based on the total mass of the compounds of the formulae I and II.

The invention also provides a process for preparing 4-tert-butylbenzaldehyde of the formula IX

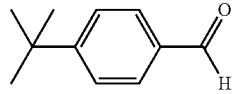
IX with less than 0.5% by weight, preferably less than 0.1% by weight, content of 3-tert-butylbenzaldehyde of the formula X

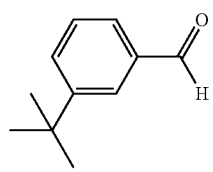
X based on the total mass of the compounds of the formulae IX and X,
starting from 4-tert-butyltoluene of the formula III

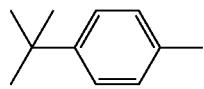
III with at most 5% by weight, preferably from 0.01 to 5% by weight, in particular from 0.1 to 5% by weight, in particular 0.5 to 5% by weight, content of 3-tert-butyltoluene of the formula IV

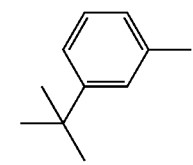
IV based on the total mass of the compounds of the formulae III and IV, as starting material,
comprising the steps of:
a) electrochemical anodic methoxylation of a mixture comprising compounds of the formulae III and IV, and also comprising the benzyl ethers of the formulae V and VI which are produced as intermediates

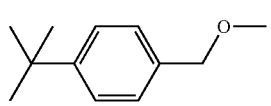
V

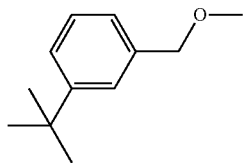
VI to give the dimethyl acetals of the formulae VII and VIII

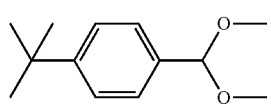
VII

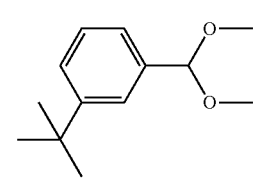
VIII in an electrolysis solution comprising methanol, at least one conducting salt, and also optionally one cosolvent or a plurality of various cosolvents;
b) hydrolysis of the mixture the dimethyl acetals of the formulae VII and VIII formed in step a) to give the corresponding benzaldehydes of the formulae IX and X

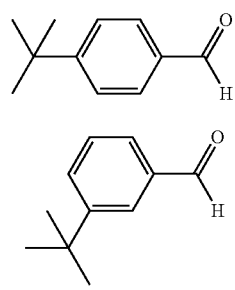
IX

X and then use of distillation to reduce the concentration of the benzaldehyde of the formula X;
where the distillation in step b) is carried out in two stages,
by using a 1st distillation column in a first distillation to remove, at the top of the 1st distillation column, a distillate which comprises more than 80% by weight of a mixture composed of unreacted starting materials of the formulae III and IV, and also of the benzyl ethers of the formulae V and VI produced as intermediates in step a), and of the benzaldehyde of the formula X,

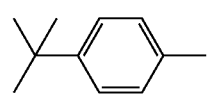
III

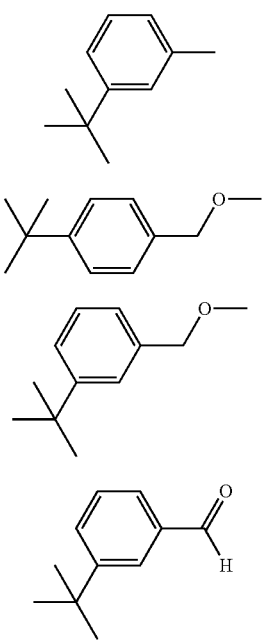

and using a 2nd distillation column in a second distillation to remove, at the top of the 2nd distillation column, the benzaldehyde of the formula IX

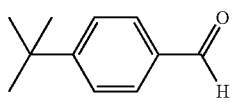

with less than 0.5% by weight, preferably less than 0.1% by weight, content of the benzaldehyde of the formula X, based on the total mass of the compounds of the formulae IX and X, from the bottom product of the first distillation, and where optionally the distillate which is obtained at the top of the 1st distillation column and which comprises the compounds of the formulae III, IV, V, VI, and X, is reused in step a) together with the 4-tert-butyltoluene of the formula III that is used as starting material.

Preferred embodiments of step a) have been described above.

Whereas the bottom product of the second distillation in step b) is usually discarded, the distillate obtained at the top of the 1st distillation column can be to some extent or entirely added to the mixture which, in step a), is subjected to the electrochemical, anodic methoxylation.

Preference is given to a process for producing 4-tert-butylbenzaldehyde of the formula VII where the distillate obtained in step b) at the top of the 1st distillation column is reused in step a) together with the 4-tert-butyltoluene of the formula III that is used as starting material.

If the distillate obtained in step b) at the top of the 1st distillation column is repeatedly reused in step a), there is an increase in the concentration in particular of the undesired benzaldehyde of the formula X, and moreover of the benzyl ether of the formula VI.

By way of example, gas chromatography can be used to determine the constitution of the distillate obtained at the top of the 1st distillation column.

After repeated conduct of steps a) and b), it is preferable to discard a proportion of up to 50% by weight, particularly preferably from 1 to 20% by weight, in particular from 2 to 7% by weight, of the distillate obtained at the top of the 1st distillation column.

It is particularly preferable that the discarded proportion of the distillate is composed of more than 15% by weight, in particular more than 20% by weight, of the benzyl ether of the formula VI and of the benzaldehyde of the formula X, based on the mass of the fraction.

As an alternative, the benzaldehyde of the formula X from the distillate obtained at the top of the 1st distillation column can also be removed by chemical conversion to a new substance, in particular a solid, where this differs significantly in its physical properties from the other liquid constituents of the formulae III, IV, V, and VI.

Preference is therefore further given to a process for producing 4-tert-butylbenzaldehyde of the formula IX where, after chemical conversion to a solid, the benzaldehyde of the formula X from the distillate obtained at the top of the 1st distillation column is removed from the other liquid constituents of the distillate, in particular from the compounds of the formulae III, IV, V, and VI, and then the substantially aldehyde-free purified distillate is reused in step a) together with the 4-tert-butyltoluene of the formula III that is used as starting material.

The person skilled in the art is aware, from the traditional methods for characterization and purification of liquid aldehydes via conversion of the aldehyde function, of various derivatives which are either solid at room temperature or have a solubility profile differing from that of the liquid constituents of the formulae III, IV, V, and VI. By way of example, the benzaldehyde of the formula X can be converted to a bisulfite adduct, imine, oxime, semicarbazone derivative, or hydrazone derivative solid at room temperature, and removed via known solid-liquid-separation methods, such as filtration or centrifuging. In the case of the bisulfite adduct, this can also be removed from the other hydrophobic liquid constituents of the formulae III, IV, V, and VI via dissolution in water.

Particular preference is therefore given to the process described above for producing 4-tert-butylbenzaldehyde of the formula IX in which the benzaldehyde of the formula X from the distillate obtained at the top of the 1st distillation column is removed from the other liquid constituents of the formulae III, IV, V, and VI by chemical conversion to a bisulfite adduct, imine, oxime, semicarbazone derivative, or hydrazone derivative solid at room temperature, and the substantially aldehyde-free purified distillate is then reused in step a) together with the 4-tert-butyltoluene of the formula III that is used as starting material.

The benzaldehyde of the formula IX which is obtainable by the process described above for producing 4-tert-butylbenzaldehyde of the formula IX and which has less than 0.1% by weight content of the benzaldehyde of the formula X, based on the total mass of the compounds of the formulae IX and X, can preferably be used in step c) of the process described in the introduction for producing 2-methyl-3-(4-tert-butyl-phenyl)propanal of the formula I. The embodiments preferred in the process described above for producing 4-tert-butylbenzaldehyde of the formula IX therefore also represent particularly preferred embodiments in the steps a) and b) of the process for producing 2-methyl-3-(4-tert-butylphenyl)propanal of the formula I.

3-tert-Butylbenzaldehyde of the formula X is undesired as intermediate in the production of 2-methyl-3-(4-tert-butylphenyl)propanal.

However, 3-tert-butylbenzaldehyde of the formula X represents a useful starting material for other syntheses, since it is difficult to obtain the 1,3-substitution pattern. The removal, purification, and use elsewhere, or marketing, of that compound therefore increases the cost-effectiveness of the present overall process.

It is possible to obtain the aldehyde of the formula X in a purity of at least 80% by weight via retrocleavage of the solid which can be obtained after removal from the other liquid constituents of the distillate.

The present invention therefore also provides a process for preparing the benzaldehyde of the formula X

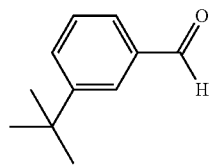

X in at least 80% by weight purity, comprising the steps of:
i) chemical conversion of the benzaldehyde of the formula X which is comprised within the distillate obtained at the top of the 1st distillation column as described above, into a solid;
ii) removal of the solid formed in step i) from the other liquid constituents of the distillate, in particular the compounds of the formulae III, IV, V, and VI;
iii) liberation of the benzaldehyde of the formula X from the solid removed in step ii).

Preference is given to a process for producing the benzaldehyde of the formula X as described above where, in step i), the benzaldehyde of the formula X is converted to a bisulfite adduct, imine, oxime, semicarbazone derivative, or hydrazone derivative solid at room temperature, the hydrazone derivative, semicarbazone derivative, oxime, imine, or bisulfite adduct formed in step i) is removed, in step ii), from the other liquid constituents of the distillate, in particular from the compounds of the formulae III, IV, V, and VI, and, in step iii), the benzaldehyde of the formula X is liberated from the hydrazone derivative, semicarbazone derivative, oxime, imine, or bisulfite adduct removed in step ii).

If the benzaldehyde of the formula X is removed in the form of a hydrazone derivative, of a semicarbazone derivative, of the oxime, of an imine, or of the bisulfite adduct, from the distillate which is obtained as described above at the top of the 1st distillation column, it is also possible to conduct further operations with one of said derivatives without liberating the 3-tert-butylbenzaldehyde of the formula X therefrom. If the compound to be synthesized is, for example, 3-tert-butylbenzylamine, the 3-tert-butylbenzaldehyde of the formula X is removed in the form of 3-tert-butylbenzaldehyde imine from the other constituents of the distillate from the 1st distillation column, of the formulae III, IV, V, and VI, and the 3-tert-butylbenzaldehyde imine is reduced by familiar methods to give 3-tert-butylbenzylamine.

A particular feature of the process of the invention for producing 2-methyl-3-(4-tert-butylphenyl)propanal of the formula I is that it can be integrated with ease into an existing process, without any need to make any change in the main raw materials, i.e. the purity of the 4-tert-butyltoluene starting material of the formula III, or any requirement to change the principles of the synthetic method used. Another feature of the process of the invention for producing 4-tert-butylbenzaldehyde of the formula IX is, as described above, that it can be integrated with ease into an existing process, without any need to make any change in the main raw materials or in the requirement to change the principles of the synthetic method used.

The distillation carried out in step b) of the process of the invention for producing 2-methyl-3-(4-tert-butylphenyl)propanal of the formula I, and in the process of the invention for producing 4-tert-butylbenzaldehyde of the formula IX, in particular the two-stage distillation, where this serves to reduce the concentration of 3-tert-butylbenzaldehyde of the formula X during production of high-priority 4-tert-butylbenzaldehyde of the formula IX, provides cost-effective access to high-purity 2-methyl-3-(4-tert-butylphenyl)propanal of the formula I, together with the possibility of obtaining 3-tert-butylbenzaldehyde of the formula X, which is not readily accessible by other means.

The examples below illustrate the invention but do not restrict the same.

Comparative Example 1

Preparation of a Mixture Comprising 98.5% by Weight of 2-methyl-3-(4-tert-butylphenyl)propanal and from 0.7 to 1.5% by Weight of 2-methyl-3-(3-tert-butylphenyl)propanal Step 1.1.—Synthesis of the Tert-Butylbenzaldehyde Dimethyl Acetals (VII) and (VIII)

A mixture composed of 22% by weight of tert-butyltoluene with 96% by weight content of 4-tert-butyltoluene (III) and 3% by weight of 3-tert-butyltoluene (IV), 77.5% by weight of methanol as solvent, and 0.5% by weight of sulfuric acid as conducting salt was electrolyzed in a continuously operated reactor in a capillary cell on graphite electrodes at a temperature of from 45° C. to 60° C. and at a current density of 42 A/dm$^2$ until the content of 4-tert-butylbenzaldehyde dimethyl acetal (VII) in the reaction mixture was about 14% by weight.

When step 1.1 was repeated, the electrolysis was carried out at temperatures of from 45° C. to 60° C., and the content of 4-tert-butylbenzaldehyde dimethyl acetal (VII) achieved in the reaction mixture was from 12 to 16% by weight.

Step 1.2.—Hydrolysis of the Tert-Butylbenzaldehyde Dimethyl Acetals (VII) and (VIII) to Give the tert-butylbenzaldehydes (IX) and (X) and Distillative Purification For work-up, reaction mixture was continuously discharged from the electrolysis cell and replaced by a fresh reaction mixture composed of 22% by weight of tert-butyltoluene with 96% by weight content of 4-tert-butyltoluene and 3% by weight of 3-tert-butyltoluene, 77.5% by weight of methanol as solvent, and 0.5% by weight of sulfuric acid as conducting salt. The methanol solvent was removed by distillation, and the remaining crude acetal was hydrolyzed with water. Phase separation gave a crude product which comprised not only 4- and 3-tert-butylbenzaldehyde but also unreacted 3- and 4-tert-butyltoluene, and also 3- and 4-tert-butylbenzyl methyl ether as returnable intermediates. Distillative work-up was carried out in two stages (distillation column 1, distillation column 2). A highly effective column with about 60 theoretical plates was used as distillation column 1.

First, the lower-boiling-point 3- and 4-tert-butyltoluene, and also 3- and 4-tert-butylbenzyl methyl ether (V and VI) were removed at the top of distillation column 1 (temperature profile: $T_{Bottom}=158.5°$ C., $T_{Top}=142°$ C. at 35 mbar) and returned (see step 1.3.) to the electrolysis.

The bottom product which came from distillation column 1 and which comprised 3-tert-butylbenzaldehyde (X), 4-tert-butylbenzaldehyde (IX), and also high boilers, was passed to distillation column 2. In distillation column 2, the 4- and 3-tert-butyl-benzaldehydes were separated at the top from the high-boiling-point contaminants, and introduced to the condensation process using propanal (see step 1.4.). The bottom product from distillation column 2 was discarded.

The distillation was carried out in such a way as to give a tert-butylbenzaldehyde composed of 97% by weight of 4-tert-butylbenzaldehyde (IX) and 1.5% by weight of 3-tert-butylbenzaldehyde (X).

Step 1.3.—Return of Product from Top of Distillation Column 1

The product produced at the top of distillation column 1 was returned to the synthesis (step 1.1.).

Step 1.4.—Subsequent Stages

The subsequent steps were carried out as described in WO 2001/027061. This gave a 2-methyl-3-(tert-butylphenyl)propanal which comprised about 98.5% by weight of 2-methyl-3-(4-tert-butylphenyl)propanal and about 1.1% by weight of 2-methyl-3-(3-tert-butylphenyl)propanal.

Repeated conduct of the synthesis described in comparative example 1 gave mixtures which respectively comprised about 98.5% by weight of 2-methyl-3-(4-tert-butylphenyl)propanal and from 0.7 to 1.5% by weight of 2-methyl-3-(3-tert-butylphenyl)propanal.

Inventive Example 2

Preparation of 4-tert-butylbenzaldehyde with High Isomeric Purity

Step 2.1.—Synthesis of the Tert-Butylbenzaldehyde Dimethyl Acetals (VII) and (VIII)

The synthesis was carried out by analogy with that in comparative example 1, step 1.1. The same starting materials were used.

Step 2.2.—Hydrolysis of the Tert-Butylbenzaldehyde Dimethyl Acetals (VII) and (VIII) to Give the Tert-Butylbenzaldehydes (IX) and (X) and Distillative Purification For work-up, reaction mixture was continuously discharged from the electrolysis cell and replaced by a fresh reaction mixture. The solvent was removed by distillation and the remaining crude acetal was hydrolyzed with water. Phase separation gave a crude product which comprised not only 4- and 3-tert-butylbenzaldehyde but also unreacted 3- and 4-tert-butyltoluene, and also 3- and 4-tert-butylbenzyl methyl ether as returnable intermediates. Distillative work-up was carried out in two stages (distillation column 1, distillation column 2). Distillation column 1 is a highly effective column with about 60 theoretical plates.

First, the lower-boiling-point 3- and 4-tert-butyltoluene, 3- and 4-tert-butylbenzyl methyl ether, and also 3-tert-butylbenzaldehyde were removed at the top of distillation column 1 (temperature profile: $T_{Bottom}=159°$ C., $T_{Top}=147°$ C. at 35 mbar) and returned (see step 2.3.) to the electrolysis; 4-tert-butylbenzaldehyde was within the bottom product of distillation column 1 here.

The bottom product which was produced by distillation column 1 and which in particular comprised 4-tert-butylbenzaldehyde, and also high boilers, was passed to distillation column 2.

In distillation column 2, 4-tert-butylbenzaldehyde (IX) was separated at the top from the high-boiling-point contaminants, and introduced to the condensation process using propanal (see step 2.4.). The bottom product from distillation column 2 was discarded. The distillation was carried out in such a way as to give a tert-butylbenzaldehyde composed of from 98 to 99% by weight of 4-tert-butylbenzaldehyde (IX) and from 0.02 to 0.08% by weight of 3-tert-butylbenzaldehyde (X).

Step 2.3.—Return of the Product from the Top of Distillation Column 1

The product produced at the top of distillation column 1 was returned to the synthesis (step 2.1.). Since after repeated conduct of steps 2.1 and 2.2, the returned product from the top of distillation column 1 comprises increasing amounts of 3-tert-butylbenzaldehyde (X), and since 3-tert-butylbenzaldehyde cannot be separated distillatively from 4-tert-butylbenzyl methyl ether (V), a small portion (from 2 to 7% by weight) of the product from the top of distillation column 1 was removed and discarded.

Step 2.4.—Subsequent Stages

The subsequent steps were carried out as described in WO 2001/027061. This gave a 2-methyl-3-(tert-butylphenyl)propanal which was composed of >99.0% by weight of 2-methyl-3-(4-tert-butylphenyl)propanal and <0.05% by weight of 2-methyl-3-(3-tert-butylphenyl)propanal.

Example 3

Preparation of 4-Tert-Butylbenzaldehyde with High Isomeric Purity Using the Conducting Salts Methyltributylammonium Methyl Sulfate (MTBS)

Step 3.1.—Synthesis of the Tert-Butylbenzaldehyde Dimethyl Acetals (VII) and (VIII)

A mixture composed of 23% by weight of tert-butyltoluene with 96% by weight content of 4-tert-butyltoluene (III) and 3% by weight of 3-tert-butyltoluene (IV), 74% by weight of methanol as solvent, and 3.0% by weight of methyltributylammonium methyl sulfate (MTBS) as conducting salt was electrolyzed in a continuously operated reactor in a capillary cell on graphite electrodes at a temperature of from 45° C. to 60° C. and at a current density of 22 A/dm², until the content of 4-tert-butylbenzaldehyde dimethyl acetal (VII) in the reaction mixture was about 14% by weight.

When step 3.1 was repeated, the electrolysis was carried out at temperatures of from 45° C. to 60° C., and the content of 4-tert-butylbenzaldehyde dimethyl acetal (VII) achieved in the reaction mixture was from 12 to 16% by weight.

Step 3.2.—Hydrolysis of the Tert-Butylbenzaldehyde Dimethyl Acetals (VII) and (VIII) to Give the Tert-Butylbenzaldehydes (IX) and (X) and Distillative Purification For work-up, reaction mixture was continuously discharged from the electrolysis cell and replaced by a fresh reaction mixture. The solvent was removed by distillation and, in order to remove the conducting salt MTBS, total vaporization was carried out in vacuo in a thin-film evaporator at from 180° C. to 220° C. and at from 10 mbar to 20 mbar. The non-vaporizable MTBS was returned to the electrolysis (step 3.1.). The crude acetal was condensed and hydrolyzed with water. Phase separation gave a crude product which comprised not only 4- and 3-tert-butylbenzaldehyde but also unreacted 3- and 4-tert-butyltoluene, and also 3- and 4-tert-butylbenzyl methyl ether as returnable intermediates. Distillative work-up was carried out in two stages (distillation column 1, distillation column 2), as in step 2.2.

Step 3.3.—Return of Product from the Top of Distillation Column 1

Conduct as in step 2.3.

Step 3.4.—Subsequent Stages

Conduct as in step 2.4.

Batchwise electrolysis to prepare 4-tert-butylbenzaldehyde dimethyl acetal (VII)

Apparatus: Undivided through-flow cell with 11 circular graphite electrodes (SGL MKUS F04, separation: 1 mm, 10 gaps), containing about 3 g of electrolyte Electrolyte: 600 g (20% by weight) of overhead product from distillation column 1 (see step 2.3 in example 2 (comprising up to 20.1% by weight of 3-tert-butylbenzaldehyde), 2390 g (79.6% by weight) of MeOH, 10.5 g of concentrated sulfuric acid (0.35% by weight, content >96%), and also a variable proportion of trimethyl orthoformate (unless otherwise stated)

Electrolysis to full conversion of 4-tert-butyltoluene (III), determined by gas chromatography Current density: 3.4 A dm$^{-2}$ (unless otherwise stated).

Temperature: 53° C. (unless otherwise stated).

The constitution of main components in the overhead product used from distillation column 1 is shown in Table B-1 (data in GC area %, input weight 600 g). The balance making up 100% in the GC area % values involves auxiliary components not defined in any more detail. To the extent that trimethyl orthoformate (TMOF) was added to the electrolyte, the proportion of methanol in the electrolyte was reduced by the same value, i.e. the total of methanol content and TMOF content in the electrolyte is constant. In order to balance the examples, the stated GC area % values are equated to GC % by weight values, thus giving the calculated proportions by weight specified in Table B-1 for main components. The end point selected for the electrolysis process was complete conversion of 4-tert-butyltoluene (III), and this was determined by means of gas chromatography. The stated amount of electrical charge required for complete conversion of III is calculated from the electrolysis time multiplied by the current intensity and the number of electrolysis gaps in the capillary gap cell used. Once the electrolysis process has ended, the electrolysis products were freed from MeOH by distillation, and the residue was distilled in order to determine the yields. Table B-1 states the weights thus found for main components, calculated from the gas chromatograms of the individual distillation fractions.

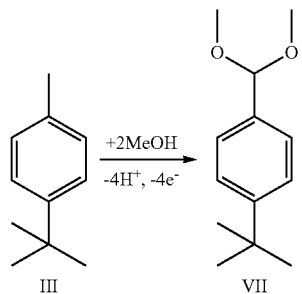

Example 4 describes the reference experiment in this series of experiments, without addition of trimethyl orthoformate (TMOF) to the electrolyte. Complete conversion of III is achieved after 495 Ah and gives 11.2 g of 4-tert-butylbenzaldehyde (IX), and also 254.0 g of 4-tert-butylbenzaldehyde dimethyl acetal (VII), which can be converted into 4-tert-butylbenzaldehyde (IX) by hydrolysis using processes described above.

Example 5 describes the effect of 1% by weight of TMOF in the electrolyte. Complete conversion of III is achieved after 387 Ah and gives 6.9 g of 4-tert-butylbenzaldehyde (IX), and also 287 g of 4-tert-butylbenzaldehyde dimethyl acetal (VII), which can be converted into IX by hydrolysis using processes described above.

Example 6 describes the effect of 2% by weight of TMOF in the electrolyte. Complete conversion of III is achieved after 333 Ah and gives 2.4 g of 4-tert-butylbenzaldehyde (IX), and also 320.8 g of 4-tert-butylbenzaldehyde dimethyl acetal (VII), which can be converted into IX by hydrolysis using processes described above.

Example 7 describes the effect of 3% by weight of TMOF in the electrolyte. Complete conversion of III is achieved after 306 Ah and gives 0.8 g of 4-tert-butylbenzaldehyde (IX), and also 334.5 g of 4-tert-butylbenzaldehyde dimethyl acetal (VII), which can be converted into IX by hydrolysis using processes described above.

Example 8 describes the effect of 3.5% by weight of TMOF in the electrolyte. This corresponds approximately to one molar equivalent, based on the amount of 3-tert-butylbenzaldehyde used in the electrolysis process. Complete conversion of III is achieved after 293 Ah and gives 0.6 g of 4-tert-butylbenzaldehyde (IX), and also 338.0 g of 4-tert-butylbenzaldehyde dimethyl acetal (VII), which can be converted into IX by hydrolysis using processes described above.

Example 9 describes the effect of 4% by weight of TMOF in the electrolyte. Complete conversion of III is achieved after 288 Ah and gives 0.7 g of 4-tert-butylbenzaldehyde (IX), and also 337.5 g of 4-tert-butylbenzaldehyde dimethyl acetal (VII), which can be converted into IX by hydrolysis using processes described above.

Example 10 describes the effect of 4.5% by weight of TMOF in the electrolyte. Complete conversion of III is achieved after 279 Ah and gives 0.6 g of 4-tert-butylbenzaldehyde (IX), and also 344.1 g of 4-tert-butylbenzaldehyde dimethyl acetal (VII), which can be converted into IX by hydrolysis using processes described above.

Example 11 describes the effect of 5.5% by weight of TMOF in the electrolyte. Complete conversion of III is achieved after 279 Ah and gives 0.6 g of 4-tert-butylbenzaldehyde (IX), and also 339.2 g of 4-tert-butylbenzaldehyde dimethyl acetal (VII), which can be converted into IX by hydrolysis using processes described above.

Example 12 describes the use, in the electrochemical methoxylation process, of a electrolyte predried over molecular sieve. Before commencement of the electrolysis process, the electrolyte was dried over molecular sieve (30 g of molecular sieve per 100 g of electrolyte) from Grace (Sylobead 564 C, 3 Å, activated at 180° C./3 mbar), until the water content reached was <0.05% by weight. The molecular sieve was removed from the electrolyte by filtration in an inert-gas atmosphere, and the electrolyte was converted under the abovementioned experimental conditions after addition of a further 9 g of concentrated sulfuric acid. Complete conversion of III is achieved after 293 Ah and gives 0.7 g of 4-tert-butylbenzaldehyde (IX), and also 355.6 g of 4-tert-butylbenzaldehyde dimethyl acetal (VII), which can be converted into IX by hydrolysis using processes described above.

with less than 0.3% by weight content of 2-methyl-3-(3-tert-butylphenyl)propanal of the formula II

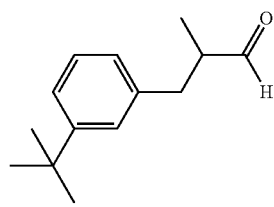

TABLE B-1

Overview of experimental results for batchwise preparation of 4-tert-butylbenzaldehyde dimethyl acetal (VII).

| | Constitution "Overhead product from column 1" | | Ex 4 without TMOF addition | Ex 5 1% of TMOF | Ex 6 2% of TMOF | Ex 7 3% of TMOF | Ex 8 3.5% of TMOF |
|---|---|---|---|---|---|---|---|
| | GC area % | Weight in g | Weight in g | Weight in g | Weight in g | Weight in g | Weight in g |
| Total in g | 88.8 | 532.7 | 434.3 | 474.8 | 511.7 | 528.1 | 530.7 |
| 3-tert-butyltoluene | 3.0 | 17.8 | 2.7 | 2.2 | 2.3 | 2.1 | 1.8 |
| 4-tert-butyltoluene | 16.9 | 101.6 | 0.2 | 0.2 | 0.1 | 0.0 | 0.2 |
| 3-tert-butylbenzyl methyl ether | 5.3 | 31.9 | 21.6 | 19.4 | 18.9 | 21.4 | 16.5 |
| 4-tert-butylbenzyl methyl ether | 40.9 | 245.2 | 13.1 | 14.5 | 13.0 | 13.5 | 10.8 |
| 3-tert-butylbenzaldehyde | 20.1 | 120.6 | 4.0 | 2.3 | 0.5 | 0.0 | 0.0 |
| 4-tert-butylbenzaldehyde | 2.0 | 12.2 | 11.2 | 6.9 | 2.4 | 0.8 | 0.6 |
| 3-tert-butylbenzaldehyde dimethyl acetal | 0.6 | 3.4 | 127.4 | 142.3 | 153.7 | 155.8 | 162.7 |
| 4-tert-butylbenzaldehyde dimethyl acetal | 0.0 | 0.0 | 254.0 | 287.0 | 320.8 | 334.5 | 338.0 |
| Electrical charge in Ah | | | 495 | 387 | 333 | 306 | 293 |

| | Constitution "Overhead product from column 1" | | Ex 9 4% of TMOF | Ex 10 4.5% of TMOF | Ex 11 5.5% of TMOF | Ex 12 Molecular sieve |
|---|---|---|---|---|---|---|
| | GC area % | Weight in g | Weight in g | Weight in g | Weight in g | Weight in g |
| Total in g | 88.8 | 532.7 | 533.7 | 542.4 | 537.8 | 557.5 |
| 3-tert-butyltoluene | 3.0 | 17.8 | 2.0 | 2.5 | 2.6 | 2.3 |
| 4-tert-butyltoluene | 16.9 | 101.6 | 0.0 | 0.1 | 0.1 | 0.1 |
| 3-tert-butylbenzyl methyl ether | 5.3 | 31.9 | 19.9 | 19.9 | 20.7 | 22.2 |
| 4-tert-butylbenzyl methyl ether | 40.9 | 245.2 | 12.4 | 13.1 | 15.3 | 12.9 |
| 3-tert-butylbenzaldehyde | 20.1 | 120.6 | 0.0 | 0.0 | 0.0 | 0.0 |
| 4-tert-butylbenzaldehyde | 2.0 | 12.2 | 0.7 | 0.6 | 0.6 | 0.7 |
| 3-tert-butylbenzaldehyde dimethyl acetal | 0.6 | 3.4 | 161.1 | 162.2 | 159.4 | 163.5 |
| 4-tert-butylbenzaldehyde dimethyl acetal | 0.0 | 0.0 | 337.5 | 344.1 | 339.2 | 355.6 |
| Electrical charge in Ah | | | 288 | 279 | 279 | 293 |

The invention claimed is:

1. A process for preparing 2-methyl-3-(4-tert-butylphenyl)propanal of the formula I based on the total mass of the compounds of the formulae I and II starting from 4-tert-butyltoluene of the formula III

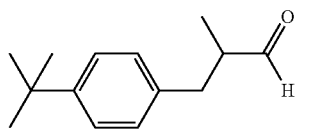

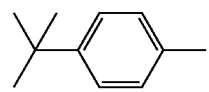

with at most 5% by weight content of 3-tert-butyltoluene of the formula IV

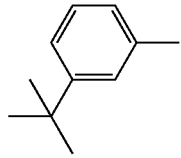

IV based on the total mass of the compounds of the formulae III and IV, as starting material, comprising the steps of:

a) electrochemical anodic methoxylating a mixture comprising compounds of the formulae III and IV, and further comprising benzyl ethers of the formulae V and VI which are produced as intermediates

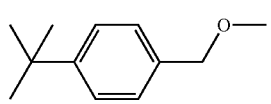

V

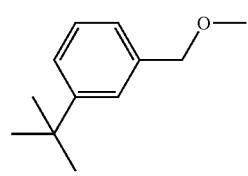

VI to form dimethyl acetals of the formulae VII and VIII

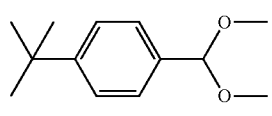

VII

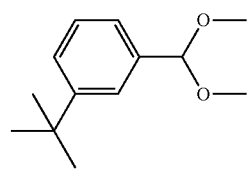

VIII in an electrolysis solution comprising methanol, at least one conducting salt, and also optionally one cosolvent or a plurality of various cosolvents;

b) hydrolyzing the mixture of the dimethyl acetals of the formulae VII and VIII formed in step a) to give corresponding benzaldehydes of the formulae IX and X

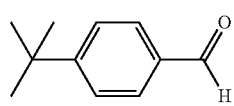

IX

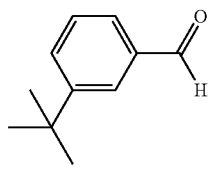

X and then using distillation to reduce the concentration of the benzaldehyde of the formula X;

c) reacting the mixture of the benzaldehydes of the formulae IX and X obtained in step b), wherein the mixture comprises less than 0.5% by weight of the benzaldehyde of the formula X, with propanal under basic conditions to give dehydrocinnamaldehydes of the formulae XI and XII;

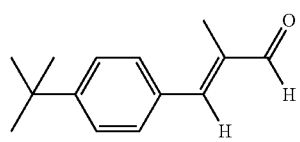

XI

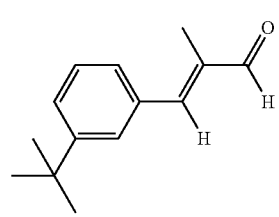

XII d) catalytic hydrogenating the dehydrocinnamaldehydes of the formulae XI and XII prepared in step c) to give propanals of the formulae I and II,

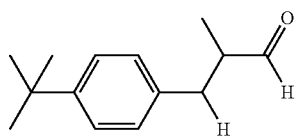

I

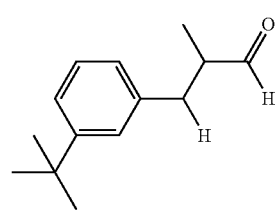

II wherein the content of the propanal of the formula II is less than 0.3% by weight, based on the total mass of the compounds of the formulae I and II, optionally with subsequent use of distillation to remove solvent residues, precursors, and byproducts;

e) optionally distilling the propanals of the formulae I and II obtained in step d), in order to reduce the concentration of the propanal of the formula II.

2. The process according to claim 1, wherein the 4-tert-butyltoluene of the formula III used as starting material in step a) has from 2 to 4% by weight content of 3-tert-butyltoluene of the formula IV, based on the total mass of the compounds of the formulae III and IV.

3. The process according to claim 1, wherein the mixture of the benzaldehydes of the formulae IX and X obtained after the distillation in step b) has less than 0.1% by weight content of the benzaldehyde of the formula X, based on the total mass of the compounds of the formulae IX and X.

4. The process according to claim 1, wherein the distillation in step b) is carried out in two stages, by using a 1st distillation column in a first distillation to remove, at the top of the 1st distillation column, a distillate which comprises more than 80% by weight of a mixture composed of unreacted starting materials of the formulae III and IV, and also of the benzyl ethers of the formulae V and VI produced as intermediates in step a), and of the benzaldehyde of the formula X,

III

IV

V

VI

X and using a 2nd distillation column in a second distillation to remove, at the top of the 2nd distillation column, the benzaldehyde of the formula IX

IX with less than 0.1% by weight content of the benzaldehyde of the formula X, based on the total mass of the compounds of the formulae IX and X, from the bottom product of the first distillation, and where optionally the distillate which is obtained at the top of the 1st distillation column and which comprises the compounds of the formulae III, IV, V, VI, and X is reused in step a) together with the 4-tert-butyltoluene of the formula III that is used as starting material.

5. The process according to claim 3, wherein the 1st distillation column used in step b) has more than 50 theoretical plates.

6. The process according to claim 1, wherein the mixture of the propanals of the formulae I and II obtained after the distillation in step d) or e) has less than 0.05% by weight content of the propanal of the formula II, based on the total mass of the compounds of the formulae I and II.

7. A process for preparing 4-tert-butylbenzaldehyde of the formula IX

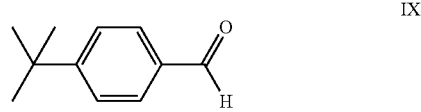

IX with less than 0.5% by weight content of 3-tert-butylbenzaldehyde of the formula X

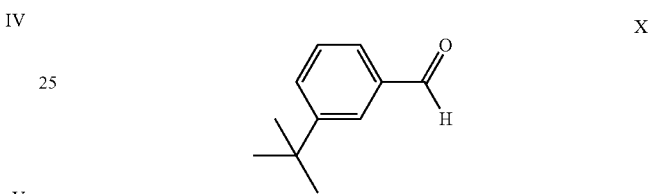

X based on the total mass of the compounds of the formulae IX and X,
starting from 4-tert-butyltoluene of the formula III

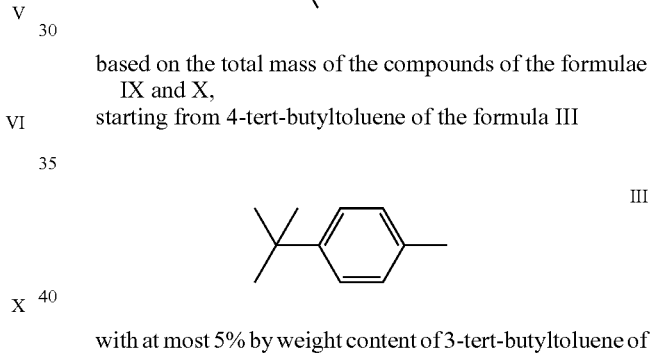

III with at most 5% by weight content of 3-tert-butyltoluene of the formula IV

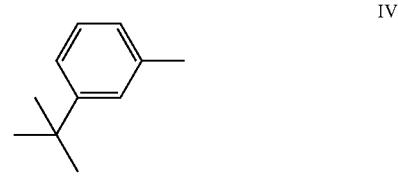

IV based on the total mass of the compounds of the formulae III and IV, as starting material,
comprising the steps of:
a) electrochemical anodic methoxylating a mixture comprising compounds of the formulae III and IV, and further comprising benzyl ethers of the formulae V and VI which are produced as intermediates

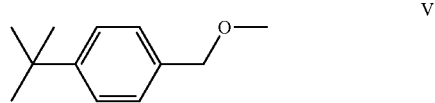

V

-continued

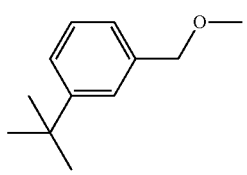

VI to give dimethyl acetals of the formulae VII and VIII

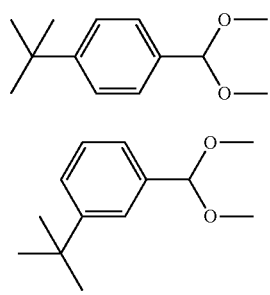

VII

VIII in an electrolysis solution comprising methanol, at least one conducting salt, and also optionally one cosolvent or a plurality of various cosolvents;

b) hydrolysing the mixture of the dimethyl acetals of the formulae VII and VIII formed in step a) to give corresponding benzaldehydes of the formulae IX and X and then using distillation to reduce the concentration of the benzaldehyde of the formula X;

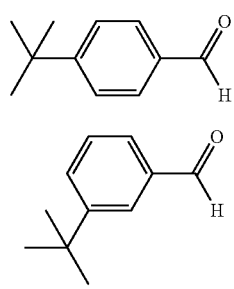

IX

X wherein the distillation in step b) is carried out in two stages, by using a 1st distillation column in a first distillation to remove, at the top of the 1st distillation column, a distillate which comprises more than 80% by weight of a mixture composed of unreacted starting materials of the formulae III and IV, and also of the benzyl ethers of the formulae V and VI produced as intermediates in step a), and of the benzaldehyde of the formula X,

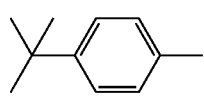

III

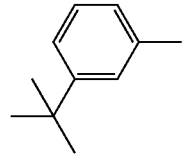

IV

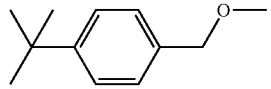

V

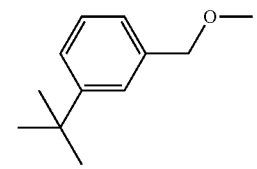

VI

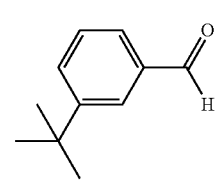

X and using a 2nd distillation column in a second distillation to remove, at the top of the 2nd distillation column, the benzaldehyde of the formula IX

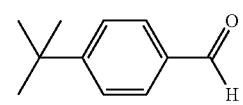

IX with less than 0.5% by weight, content of the benzaldehyde of the formula X, based on the total mass of the compounds of the formulae IX and X, from the bottom product of the first distillation, and wherein optionally, the distillate which is obtained at the top of the 1st distillation column and which comprises the compounds of the formulae III, IV, V, VI, and X, is reused in step a) together with the 4-tert-butyltoluene of the formula III that is used as starting material.

8. The process according to claim 7, wherein the distillate obtained at the top of the 1st distillation column is reused in step a) together with the 4-tert-butyltoluene of the formula III that is used as starting material.

9. The process according to claim 7, wherein a proportion of from 2 to 7% by weight of the distillate obtained at the top of the 1st distillation column is discarded.

10. The process according to claim 9, wherein the discarded proportion of the distillate is composed of more than 20% by weight of the benzyl ether of the formula VI and of the benzaldehyde of the formula X, based on the mass of the discarded proportion.

11. The process according to claim 7, wherein the benzaldehyde of the formula X from the distillate obtained at the top of the 1st distillation column is chemically converted to a solid and removed from the other liquid constituents of the distillate to create substantially aldehyde-free purified distillate, and then the substantially aldehyde-free purified distillate is reused in step a) together with the 4-tert-butyltoluene of the formula III that is used as starting material.

12. The process according to claim 11, wherein the benzaldehyde of the formula X is converted by chemical conversion to a bisulfate adduct, imine, oxime, semicarbazone derivative, or hydrazone derivative solid at room temperature.

13. The process according to claim 1, wherein steps a) and b) comprise
   a) electrochemical anodic methoxylating a mixture comprising compounds of the formulae III and IV, and further comprising benzyl ethers of the formulae V and VI which are produced as intermediates

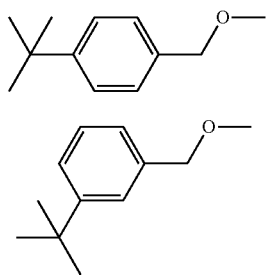

V

VI to give dimethyl acetals of the formulae VII and VIII

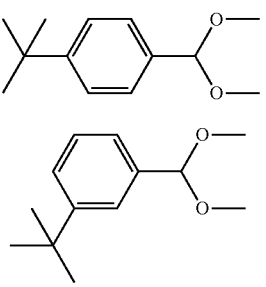

VII

VIII in an electrolysis solution comprising methanol, at least one conducting salt, and also optionally one cosolvent or a plurality of various cosolvents;
   b) hydrolysing the mixture of the dimethyl acetals of the formulae VII and VIII formed in step a) to give corresponding benzaldehydes of the formulae IX and X and then using distillation to reduce the concentration of the benzaldehyde of the formula X;

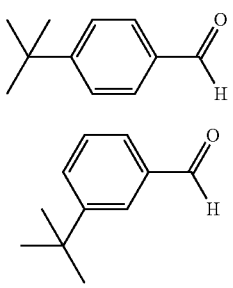

IX

X wherein the distillation in step b) is cameo out in two stages,
by using a 1st distillation column in a first distillation to remove, at the top of the 1st distillation column, a distillate which comprises more than 80% by weight of a mixture composed of unreacted starting materials of the formulae III and IV, and also of the benzyl ethers of the formulae V and VI produced as intermediates in step a), and of the benzaldehyde of the formula X,

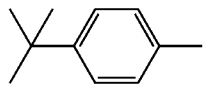

III

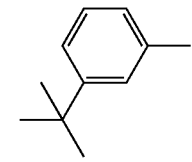

IV

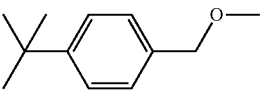

V

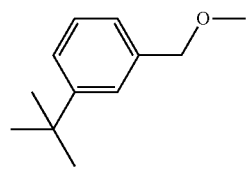

VI

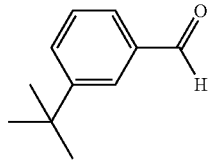

X and using a 2nd distillation column in a second distillation to remove, at the top of the 2nd distillation column, the benzaldehyde of the formula IX

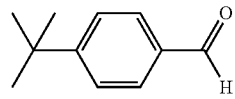

IX with less than 0.5% by weight, content of the benzaldehyde of the formula X, based on the total mass of the compounds of the formulae IX and X, from the bottom product of the first distillation, and wherein optionally, the distillate which is obtained at the top of the 1st distillation column and which comprises the compounds of the formulae III, IV, V, VI, and X, is reused in step a) together with the 4-tert-butyltoluene of the formula III that is used as starting material.

14. A process for preparing the benzaldehyde of the formula X

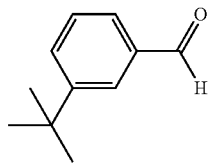

X in at least 80% by weight purity, comprising the steps of:
  i) chemically converting benzaldehyde of the formula X present in the distillate obtained at the top of the 1st distillation column according to claim 7, into a solid;
  ii) removing the solid formed in step i) from the other liquid constituents of the distillate;
  iii) liberating the benzaldehyde of the formula X from the solid removed in step ii).

15. The process according to claim 14, wherein, in step i), the benzaldehyde of the formula X is converted to a bisulfite adduct, imine, oxime, semicarbazone derivative, or hydrazone derivative solid at room temperature, the hydrazone derivative, semicarbazone derivative, oxime, imine, or bisulfate adduct formed in step i) is removed, in step ii), from the other liquid constituents of the distillate and, in step iii), the benzaldehyde of the formula X is liberated from the hydrazone derivative, semicarbazone derivative, oxime, imine, or bisulfite adduct removed in step ii).

16. The process according to claim 1, wherein the water content of the electrolysis solution in step a) is at most 20% by weight.

17. The process according to claim 1, wherein the electrolysis solution in step a) comprises from 0.1 to 10% by weight of an orthoester or a mixture of various orthoesters.

18. The process according to claim 17, wherein orthoesters comprise orthoformic esters and/or orthoacetic esters.

19. The process according to claim 18, wherein trimethyl orthoformate and/or triethyl orthoformate is/are used.

\* \* \* \* \*